(12) United States Patent
Blake et al.

(10) Patent No.: US 9,351,662 B2
(45) Date of Patent: May 31, 2016

(54) MRI SCANNER THAT OUTPUTS BONE STRENGTH INDICATORS

(75) Inventors: Andrew Blake, Stapleford (GB); Daniel Joseph Holland, Cambridge (GB); Lynn Faith Gladden, Landbeach (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 560 days.

(21) Appl. No.: 13/162,711

(22) Filed: Jun. 17, 2011

(65) Prior Publication Data

US 2012/0323110 A1 Dec. 20, 2012

(51) Int. Cl.
*A61B 5/055* (2006.01)
*A61B 5/00* (2006.01)

(52) U.S. Cl.
CPC .............. *A61B 5/055* (2013.01); *A61B 5/4509* (2013.01); *A61B 2576/02* (2013.01); *G06T 2207/10088* (2013.01); *G06T 2207/30008* (2013.01)

(58) Field of Classification Search
CPC .. A61B 5/055; A61B 5/4509; A61B 2576/02; G01R 33/20; G06T 7/0012; G06T 2207/10088; G06T 2207/30008
See application file for complete search history.

(56) References Cited

U.S. PATENT DOCUMENTS

| | | | |
|---|---|---|---|
| 6,975,894 B2 | 12/2005 | Wehrli et al. | |
| 7,664,298 B2 | 2/2010 | Lang et al. | |
| 7,783,582 B2 | 8/2010 | Doctor et al. | |
| 8,351,666 B2 * | 1/2013 | Stonefield | 382/128 |
| 2003/0175410 A1 | 9/2003 | Campbell et al. | |
| 2004/0062786 A1 * | 4/2004 | Ascenzi et al. | 424/423 |
| 2005/0010106 A1 * | 1/2005 | Lang et al. | 600/425 |
| 2005/0131662 A1 | 6/2005 | Ascenzi et al. | |
| 2006/0155186 A1 * | 7/2006 | James | 600/410 |
| 2008/0031412 A1 * | 2/2008 | Lang et al. | 378/54 |
| 2008/0119719 A1 | 5/2008 | Ascenzi et al. | |
| 2008/0171319 A1 | 7/2008 | Urdea et al. | |

OTHER PUBLICATIONS

Chan, et al., "A Bayesian Review of the Meta-Analysis on the Efficacy of Bone Marrow-Derived Cells Transplantation in Adult Patients with Heart Diseases", Retrieved at << http://www.iaeng.org/publication/WCE2009/WCE2009__pp1287-1291.pdf >>, Proceedings of the World Congress on Engineering, vol. 2, Jul. 1-3, 2009, pp. 1-5.

Holland, et al., "A Bayesian Approach to Characterising Multi-Phase Flows Using Magnetic Resonance: Application to Bubble Flows." Journal of Magnetic Resonance 209, Dec. 17, 2010, pp. 83-87.

* cited by examiner

*Primary Examiner* — Ruth S Smith
(74) *Attorney, Agent, or Firm* — Micky Minhas (57) ABSTRACT

Described herein are various technologies pertaining to diagnosing and/or prescribing treatment for osteoporosis. A bone of a patient is subjected to an MRI scan, and the resultant signal is subjected to a likelihood function. The output of the likelihood function are values that are parameters that are employed to ascertain connectivity of trabeculae in the bone of the patient and volumetric trabecular density of the bone.

20 Claims, 6 Drawing Sheets

MRI SCANNER THAT OUTPUTS BONE STRENGTH INDICATORS

BACKGROUND

Osteoporosis is defined as "a skeletal disease characterized by low bone mass and micro-architectural deterioration of bone tissue, with a consequent increase in bone fragility and susceptibility to fracture". It is a common bone disorder that significantly compromises life quality and shortens life expectancy. Currently, one third of post-menopausal women and one fifth of men over fifty years of age suffer from osteoporosis; the prevalence is expected to rise further as the population ages. Quantitative assessments of the bone strength are required both to detect osteoporosis and monitor treatments. Conventional mechanisms for detecting and monitoring osteoporosis include the measurement of the bone mineral density (BMD), with a lower BMD correlating with lower bone strength and higher fracture risk. However, studies have indicated that approximately half of the post-menopausal women with incident, low energy fractures have a BMD above the World Health Organization threshold definition of osteoporosis. Furthermore, changes in BMD following therapy explain only 4-30% of the observed fracture risk reduction. Thus, a significant amount of research has focused on examining the effect of bone microstructure on bone strength and incidence of osteoporosis; in particular the microstructure of trabecular bone as an indicator of fracture risk has been studied.

Trabecular microstructure has been shown to correlate strongly with bone strength in ex-vivo studies. Non-invasive and in vivo measurements of the trabecular structure, however, are difficult as they require 3D resolutions on the order of 50 $\mu m^3$. Several techniques have been used to study the microstructure of bone in vivo including radiographs, computed tomography (CT) and magnetic resonance imaging (MRI). These techniques, however, all have limitations in their present implementations. Radiographs provide only a projection of cortical and trabecular microstructure, and therefore only the texture of trabecular bone is resolved. CT requires considerable radiation dose and the resolution of whole body scanners is limited to ~300 $\mu m^3$; 80 $\mu m^3$ resolution is achievable in the periphery, however, peripheral bones are less critical clinically. The significant radiation exposure is particularly problematical for ongoing treatment efficacy trials. Additionally, conventional MRI systems are limited to low resolution (~300 $\mu m^3$) due to the poor signal-to-noise ratio known to correspond to such systems and the long time taken to acquire high resolution 3D data.

SUMMARY

The following is a brief summary of subject matter that is described in greater detail herein. This summary is not intended to be limiting as to the scope of the claims.

Described herein are various technologies for using magnetic resonance scan data to generate values that are indicative of strength of a trabecular bone of a patient. With more particularity, described herein are various technologies pertaining to generating values that are indicative of whether a patient suffers from osteoporosis and/or the degree to which the patient suffers from osteoporosis.

A model can be developed that is representative of the microstructure of trabecular bone. In particular, trabecular bone comprises hard bone (trabeculae) and pockets of marrow phase. When generating the model, the pockets of marrow phase can be modeled as particular three-dimensional shapes, such as spheres, ellipsoids, cylinders, cuboids, and/or the like. These three-dimensional shapes can be characterized by size, aspect ratio, and optionally orientation, and can be based at least in part upon data obtained from ex vivo experiments of trabecular bones.

Subsequent to the trabecular bone microstructure being modeled, a magnetic resonance scan of trabecular bone of the patient can be performed to obtain measurements of the trabecular bone in the Fourier domain. The magnitude of the measured Fourier samples is related to the size and aspect ratio of a pocket of marrow phase. Bayesian analysis can be utilized to output likelihood data pertaining to parameters (size, aspect ratio, and orientation of pockets of marrow phase in the trabecular bone), which in turn can be employed to generate values that are indicative of strength of the bone. These values may be, for instance, connectivity of the bone and/or volumetric trabecular density in the trabecular bone of the patient. Based at least in part upon these values, a physician can diagnose the patient with osteoporosis and/or prescribe treatment to the patient with respect to osteoporosis.

Other aspects will be appreciated upon reading and understanding the attached figures and description.

DETAILED DESCRIPTION

Various technologies pertaining to utilizing Bayesian analysis together with magnetic resonance (MR) signals to compute values that are indicative of bone strength will now be described with reference to the drawings, where like reference numerals represent like elements throughout. In addition, several functional block diagrams of exemplary systems are illustrated and described herein for purposes of explanation; however, it is to be understood that functionality that is described as being carried out by certain system components may be performed by multiple components. Similarly, for instance, a component may be configured to perform functionality that is described as being carried out by multiple components. Additionally, as used herein, the term "exemplary" is intended to mean serving as an illustration or example of something, and is not intended to indicate a preference.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Figure 1:
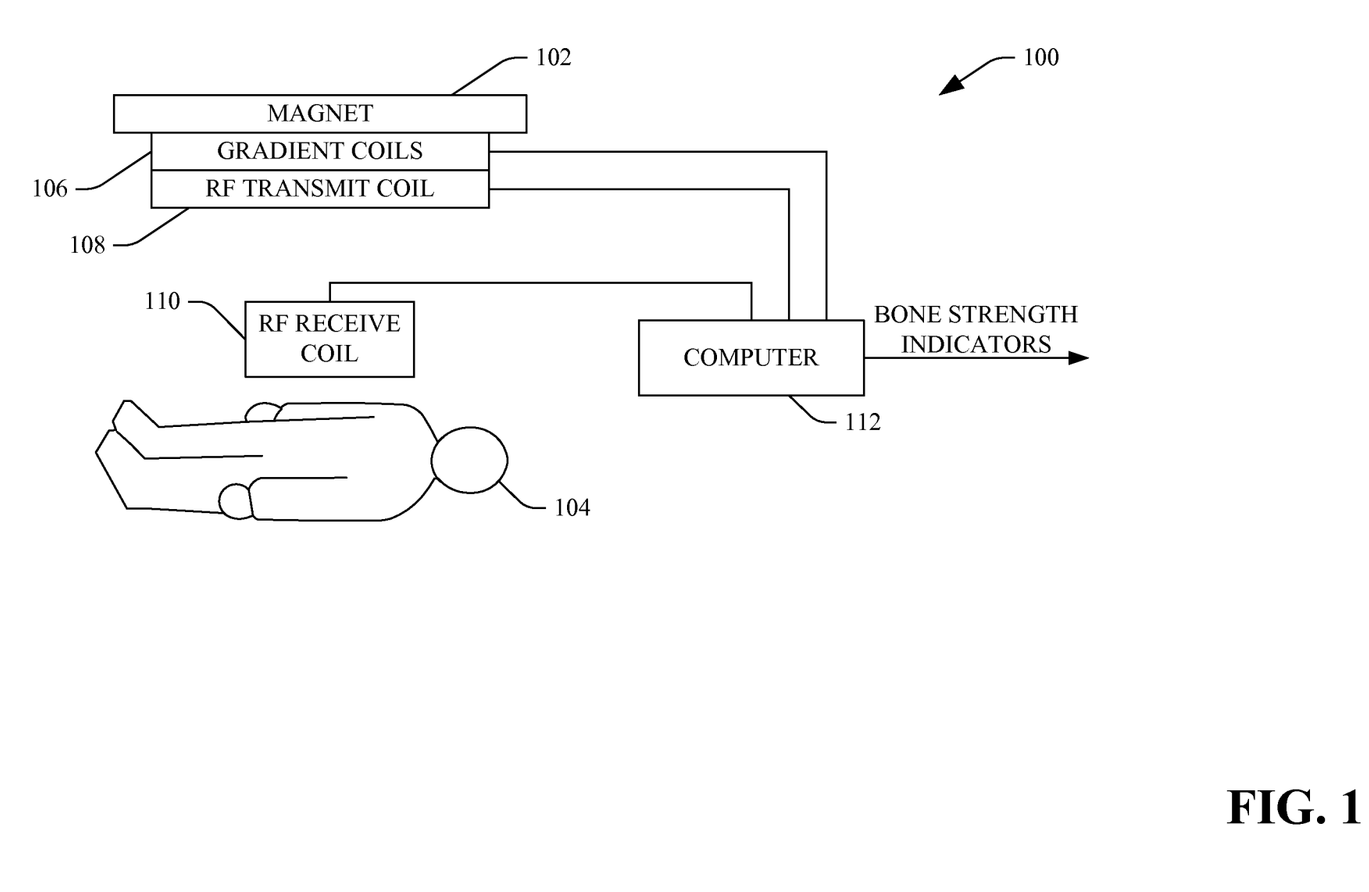
FIG. 1 is a functional block diagram of an exemplary system that facilitates computing values that are indicative of bone strength based at least in part upon data from a magnetic resonance scan of a bone of a patient.

With reference to FIG. 1, an exemplary MRI scanner 100 that facilitates computing values that are indicative of strength of a bone in a patient is illustrated. The MRI scanner 100 can be an MRI scanner installed in a hospital, research laboratory, or the like. Additionally, the MRI scanner 100 can be a portable permanent magnet MRI scanner 100. The MRI scanner 100 includes a primary magnet 102 that produces substantially homogeneous, temporally constant main magnetic field in an examination region. The primary magnet 102 is intended to encompass a magnet that generates a well-defined gradient in a magnetic field. Depending on a desired main magnetic field strength and requirements of a particular application, various magnet technologies (e.g., superconducting, resistive, or permanent magnet technologies) and physical magnet configurations (e.g., solenoidal or open magnet configurations) can be implemented.

A patient 104 may reside in the examination region, such that the MRI scanner 100 can perform a scan of a particular region of interest (e.g., a region of bone). The MRI scanner 100 additionally includes gradient coils 106 that generate time-varying gradient magnetic fields along the x, y, and z-axes of the examination region. An RF transmit coil 108 produces radio frequency signals which excite or otherwise manipulate hydrogen or other magnetic resonant active nuclei in the patient 104. In an example, the RF transmit coil can be relatively large to improve the homogeneity of the excitation.

The MRI scanner 100 additionally includes an RF receive coil 110 that is positioned proximate to a region of interest of the patient 104. The RF receive coil 110 receives magnetic resonance signals generated by the excited nuclei. While shown as being separate coils, it is to be understood that the RF transmit coil 108 and the RF receive coil 110 can be combined.

The MRI scanner 100 can further include a computer 112 that is configured to control signals provided to the gradient coils 106 and the RF transmit coil 108. Pursuant to an example, the computer 112 can control an RF source that generates an RF signal, a pulse programmer that shapes the RF signal, and an RF amplifier that amplifies the shape signal to levels required by the RF transmit coil 108 for exciting nuclei in the patient 104. The computer 112 can also control a gradient pulse programmer that establishes the shape and amplitude of the desired time-varying magnetic fields, and a gradient magnifier that amplifies the signals to levels required by the respective x, y, and z gradient coils 106. A sensor (not shown), such as an RF detector, can be in communication with the computer 112, wherein the RF detector receives and amplifies signals generated by the RF receive coil 110. Sensed signals may then be digitized by an analog to digital converter. Pursuant to an example, the RF detector can utilize heterodyning and/or direct detection of the signal at its resonant frequency.

The signals generated by the RF receive coil 110 (optionally after amplification and digitization) are received by the computer 112, which, as will be described in greater detail below, can comprise computer-executable instructions that cause the computer to generate values that are indicative of strength of the bone of the patient 104. With more specificity, the computer 112 can be programmed to utilize a likelihood function to output values that are indicative of connectivity and volumetric trabecular density in the trabecular bone. These values can be employed by a physician, for instance, to diagnose osteoporosis. In another example, these values can be employed by the physician to prescribe treatment for osteoporosis.

Figure 2:
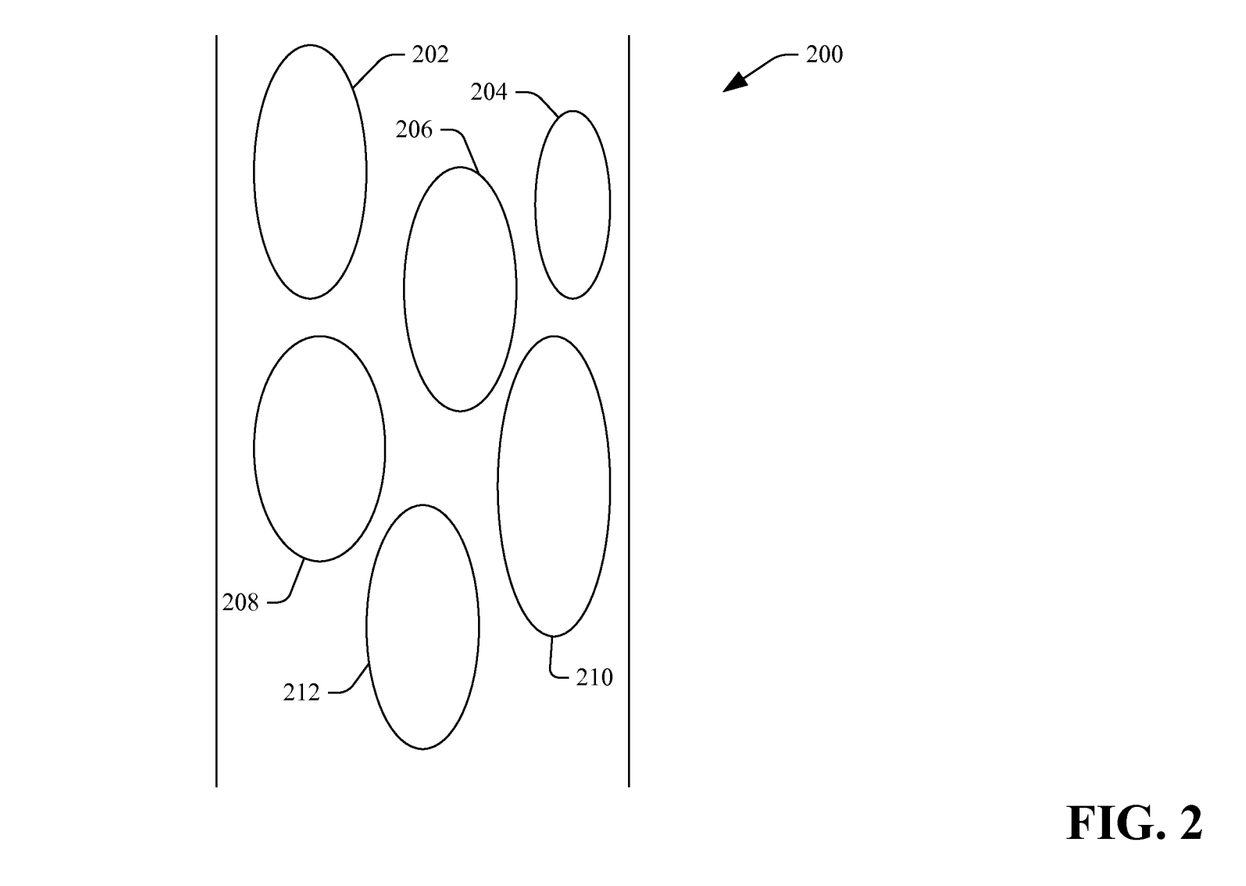
FIG. 2 illustrates an exemplary trabecular bone structure.

Turning now to FIG. 2, an exemplary illustration of a portion of a trabecular bone 200 is depicted. The trabecular bone 200 includes numerous pockets 202-212 of marrow phase. The larger the size of the pockets and/or the lower the density of pockets, generally, the weaker the strength of the bone (and thus the higher the risk of fracture). In contrast, smaller pockets and greater density of pertains to greater bone strength. The computer 112 is programmed with a likelihood function that can be evaluated over (possibly modified) signals that are generated by the RF receive coil 110, and can generate values that are indicative of most likely size, aspect ratio, and optionally orientation of the marrow phase pockets 202-212 in the trabecular bone 200. For instance, the values can be generated by the likelihood function based at least in part upon multiple scans of the trabecular bone 200 from different angles, thereby generating three-dimensional data. The computer 112 can utilize these values to compute connectivity and/or volumetric trabecular density of the trabecular bone 200. The computer 112 can then output data that is indicative of these values to a physician or technician, wherein the data is indicative of strength of the trabecular bone 200 that was subject to the MRI scan. This data can be numerical values displayed on a display screen of the computer 112, a visual indicator that indicates to the physician, technician, and/or patient 104 whether the strength of the trabecular bone 200 is sufficient (e.g., green for a healthy bone, red for a weak bone), an audible indicator that indicates to the physician, technician, and/or patient 104 whether the strength of the trabecular bone 200 is sufficient, etc.

Figure 3:
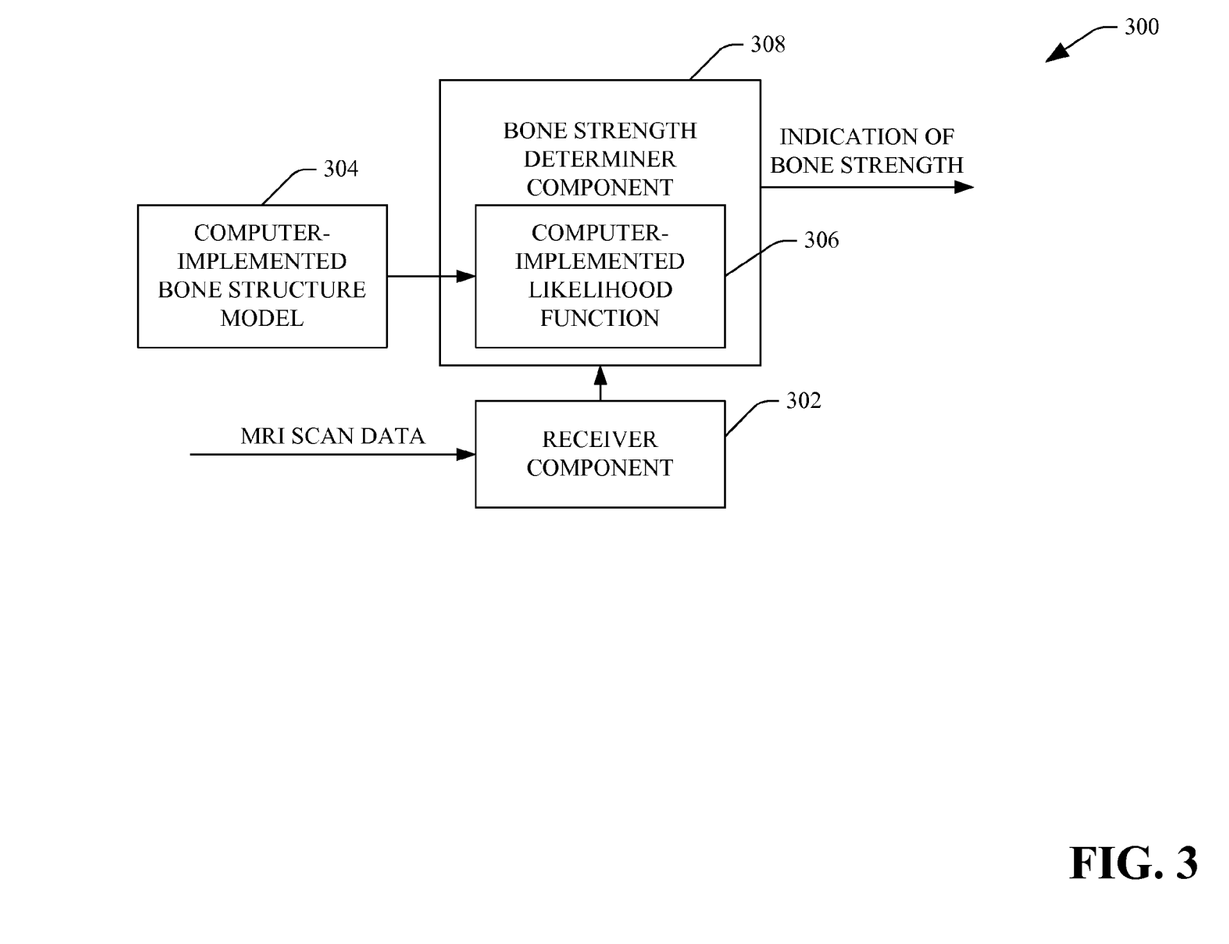
FIG. 3 is a functional block diagram of an exemplary system that facilitates computing values that are indicative of bone strength.

Now referring to FIG. 3, an exemplary system 300 that can be included in the computer 112 is illustrated, wherein the system 300 is configured to generate values that are indicative of strength of a bone. With more particularity, the system 300 can quantify the connectivity and volumetric trabecular density of trabecular bone, and such information can be by a physician to diagnose and/or prescribe treatment for osteoporosis.

The system 300 comprises a receiver component 302 that receives scan signals from the MRI scanner 100. For instance, the scan signals can be a plurality of one dimensional scans that are oriented at a variety of angles in three dimensions to characterize the three-dimensional structure of the bone. Moreover, during the scan, volume selective excitation can be employed to ensure that only signal from within the bone is excited and measured, and data from tissue surrounding the bone is not received.

The system 300 additionally includes a computer-implemented bone structure model 304, which models exemplary microstructure of bone. As described above, a trabecular bone includes pockets of marrow phase. The computer-implemented bone structure model 304 can model these pockets as ellipsoids, spheres, cuboids, cylinders, or other suitable three-dimensional shape. Based upon this bone-structure model 304, a computer-executable likelihood function 306 can be learned. A bone strength determiner component 308 can comprise the likelihood function 306, and can be in communication with the receiver component 302. Responsive to the receiver component 302 receiving MRI scan data, the bone strength determiner component 308 can cause the computer-executable likelihood function 306 to be evaluated over the scan data, resulting in computation of most likely size, aspect ratio, and/or orientation of pockets of marrow phase in the trabecular bone subjected to the scan. The bone strength determiner component 308 can compute values for connec tivity and volumetric trabecular density based upon these aforementioned parameters.

With more particularity, Bayesian analysis is utilized to quantify the size, aspect ratio, and/or orientation of marrow phase pockets in a trabecular bone. Bayesian analysis is a statistical procedure that is employed to estimate parameters of an underlying distribution based upon an observed or estimated (modeled) distribution. Exemplary employment of Bayesian analysis in connection with computing values indicative of strength of a trabecular bone based upon MRI scans of the bone is described herein.

A signal measured using magnetic resonance (MR), is governed by the following:

$$S(k)=\int \rho(x)\exp(i2\pi kx)dx, \qquad (1)$$

where $\rho(x)$ defines the image (the map of mobile $^1$H nuclei), x corresponds to the spatial position and $k=\gamma(2\pi)^{-1}\int G_x(t) dt$, where $\gamma$ is the gyromagnetic ratio and $G_x(t)$ describes the strength of the magnetic field in the x direction as a function of time t. Accordingly, the signal, S(k), and image, $\rho(x)$, are mutually conjugate Fourier pairs; hence by controlling the gradient strength as a function if time it is possible to sample any point in the spatial frequency domain of the image—referred to herein as k-space. Signals pertaining to the y and z directions are omitted for sake of brevity.

In the Bayesian approach described herein, the computer-implemented likelihood function 306 can be developed that relates the measured signal, S(k), to the state of the system β (e.g., the marrow phase pocket size, distribution, aspect ratio, and/or orientation in the trabecular bone). Described below is an example where marrow phase pockets are modeled as spheres (and accordingly, orientation is irrelevant). It is to be understood, however, that the spherical model can be replaced by models for some other suitable three-dimensional structure, such as an ellipsoid, a cuboid, a cylinder, or the like.

In Bayesian analysis, the state of a system β can be inferred from a set of observations ŷ from the posterior probability density function p(β|ŷ):

$$p(\beta|\hat{y}) \propto p(\hat{y}|\beta)p(\beta), \qquad (2)$$

where p(ŷ|β) is the likelihood function and p(β) incorporates prior knowledge. Here, it is desirable to ascertain the size of the marrow phase pockets and size distribution (assuming a known aspect ratio) in the trabecular bone, which corresponds to β, given a set of measurements, ŷ, of the signal intensity in k-space. When developing the likelihood function 306, a functional form for the size can be assumed, and parameters of the size can be estimated. Accordingly, if pockets of marrow phase are modeled as spheres, in an exemplary embodiment, the parameter that defines the size of an individual pocket is r, and the distribution of r can be characterized using two parameters: the mean radius $\bar{r}$ and a standard deviation $\sigma_r$. These two parameters can describe the state of the system β, which can be obtained as p(β|ŷ). In another exemplary embodiment, size distribution can be characterized through utilization of a multi-modal size distribution. For instance, a multi-parameter fit (e.g., a four parameter fit) with several means (e.g., two means) and several standard deviations (e.g., two standard deviations) can be employed to characterize the size distribution. Pursuant to an example, marrow phase pocket size distribution can be modeled through utilization of a distribution given by a log-normal distribution, where the log-normal distribution is defined as follows:

$$p(r, \mu, \sigma_\mu) = \frac{1}{r\sigma_\mu\sqrt{2\pi}} \exp\left(-\frac{(\ln r - \mu^2)}{2\sigma_\mu^2}\right), \qquad (3)$$

where the parameters $\mu$ and $\sigma_\mu$ uniquely define the mean $\bar{r}=\exp(\mu+\sigma_\mu^2/2)$ and variance $\sigma_r^2=\bar{r}^2(\exp(\sigma_\mu^2)-1)$ of the distribution. A calculated posterior distribution characterizes the probability distribution for the parameters $\bar{r}$ and $\sigma_r$.

The likelihood function 306 can be determined by considering how the signal intensity varies in k-space given a particular distribution of pocket sizes (and possibly shapes). Pursuant to an example, a one-dimensional image f (x) can be formed that includes the projection of N marrow phase pockets onto the x-axis. The projection of each individual pocket can be defined by the function h(r, x), where r is the characteristic size of the pocket and x is the spatial coordinate. Defining the Fourier transform of f(x) and h(r, x) as F(k) and H(r, k), respectively, the signal measured by way of MR obeys the following:

$$F(k)=\Sigma_{j=1}^{N}H(r_j,k)\exp(-2\pi kx_{c,j}) \qquad (4)$$

where $x_{c,j}$ is the location of the center of the jth pocket, and use has been made of the linearity and shift invariance of the Fourier transform. Assuming that $\{x_{c,j}\}$ is independent and identically distributed, then for a given k, the expected F(k) is 0—e.g., E(F(k))=0, and $$E(|F(k)|^2)=NE(|H(r_j,k)|^2). \qquad (5)$$

If a signal is obtained from the magnitude of a sum of complex values, each of random phase, such signal can be described by the Rayleigh distribution, provided that the number of values in the sum is sufficiently large. Therefore, in the limit of large numbers (e.g., large number N), the likelihood function describing the magnitude of the signal at any given k will be defined by a Rayleigh distribution:

$$p(|F(k)||\lambda) = \frac{F(k)}{\lambda(k)^2} \exp\left(-\frac{|F(k)|^2}{2\lambda(k)^2}\right), \qquad (6)$$

where $\lambda^2=E(|F(k)|^2)/2$. The value of N required for Eq. (6) to hold can depend upon the distribution of marrow phase pocket sizes in the trabecular bone. For pockets of a uniform size, $E(|H(r_j,k)|^2)=|H(\bar{r},k)|^2$, and therefore equation (6) holds for N≥2. For a pocket-size distribution given by a log-normal distribution, the value of N required will depend on the parameters of the distribution, and an expression similar to Eq. (6) can be derived numerically. In an example, the expression of Eq. (6) can hold for approximately N>6 for most distributions of r.

Eq. (6) defines the likelihood function for the signal as a function of $\bar{r}$ and $\sigma_r$. Therefore, if $\lambda^2$ is known for all $\bar{r}$ and $\sigma_r$, p(β|ŷ) can be obtained from Eq. (2), and this can be used to estimate β≡{$\bar{r}$, $\sigma_r$}, which characterizes the marrow phase pocket distribution. Assuming that the pockets are spherical in shape and a size distribution given by a delta function (e.g., $\sigma_r=0$ such that $r_j=\bar{r}$ for all j), an analytical expression for $H(r\cdot k)$, and therefore $\lambda$, can be obtained:

$$\lambda^2(r, k) = \frac{N}{2}\left(\frac{\sin(2\pi kr) - 2\pi kr\cos(2\pi kr)}{2\pi^2 k^3}\right)^2. \quad (7)$$

The exemplary likelihood function set forth above has been described with respect to image data in one dimension. It is ascertainable that, as a trabecular bone has a relatively complex internal geometry, a series of one-dimensional scans can be generated from the MRI scanner 100, wherein such scans are oriented at a variety of angles in three dimensions to characterize the three-dimensional structure of the bone. This enables three-dimensional models of the trabecular microstructure to be used.

Additional detail pertaining to the bone structure model 304 will now be provided. The bone structure model 304 can be an idealized model of the microstructure of trabecular bone, wherein pockets of the marrow phase can be modeled with size and/or orientation and/or distribution that corresponds to a healthy trabecular bone. Various possible shapes of bone structure can be considered, and can be utilized to characterize signal intensity from the MRI scanner 100.

In a first example, the bone structure model 304 can characterize the trabecular bone structure by its connectivity $\chi$, trabecular bone volume fraction BV/TV, and trabecular orientation $\theta$, all of which may be correlated to bone strength and can be used as indicators of osteoporosis. The marrow phase of the trabecular bone can be modeled as a collection of three-dimensional elements, including but not limited to spheres, ellipsoids, cuboids, cylinders, or the like. Building of an exemplary likelihood function with the marrow phase represented as spheres has been presented above. The three-dimensional elements can be characterized by a size r and an aspect ratio a. For instance, ellipsoids can be described by the following piecewise algorithm:

$$Ell(x, y, z) = \begin{cases} \omega & \text{for } r^{-1}x^2 + r^{-1}y^2 + (r/a)^{-1}z^2 \le 1 \\ 0 & \text{otherwise,} \end{cases} \quad (8)$$

where r is the diameter of the ellipsoid in the x and y directions, and $\omega$ corresponds to the intensity of the signal from the MRI scanner 100.

In another example, marrow phase pockets can be modeled as cuboids as follows:

$$Cub(x, y, z) = \begin{cases} \omega & \text{for } |x| \le 0.5r, |y| \le 0.5r, |z| \le 0.5(r/a) \\ 0 & \text{otherwise.} \end{cases} \quad (9)$$

In yet another example, marrow phase pockets can be modeled as cylinders as follows:

$$Cyl(x, y, z) = \begin{cases} \omega & \text{for } x^2 + y^2 \le r^2, |z| \le 0.5(r/a) \\ 0 & \text{otherwise.} \end{cases} \quad (10)$$

These shapes can be oriented at any arbitrary angle $\theta$ by applying a rotation. In addition, the variation of these parameters can be defined as r', a', and $\theta'$, respectively, which form an additional set of input parameters to the likelihood function 306. Simulations and/or experimental data can be employed to generate likelihood functions for a range of values r, a, $\theta$, r', a', and $\theta'$ that are known to exist in trabecular bone. The above-mentioned three models of marrow phase pockets can then be used (alone or in combination) to determine a most accurate representation of the range of values. For instance, cuboids and ellipsoids may be more representative of plate-like trabeculae, whereas cylinders may be more representative of rod-like trabeculae.

The result of the modeling and simulations/observations is Eq. (1), which was defined for the case of identical spheres in Eq. (7), for combinations of the aforementioned parameters. Eq. (1) can be considered a portion of a prior distribution, wherein the prior distribution may include additional information such as the probability of a particular patient having osteoporosis, the probability of a particular trabecular density, etc. The additional information can be derived from age of the patient, BMD measurements taken from the patient, related to historical measurements of the patient, or the like. The patient 104 may be scanned, and the MRI signals (mapped to the parameters) can be retained as an observed distribution. The likelihood function 306 is then evaluated over the observed distribution to generate the posterior distribution of the parameters r, a, $\theta$, r', a', and $\theta'$. Each combination of parameters also defines the expected volume of the shapes comprising the marrow phase, Ev, and therefore the number of these shapes that is present, Ns. Trabecular bone can be regarded as a multiply connected network, and therefore the number of trabeculae TbN is equal to Ns, and the connectivity of the bone x is equal to the following:

$$\chi = TbN - 1. \quad (11)$$

Similarly, the total volume of the region of interest Vt is determined by the sensitive volume of the MRI detection—which may be determined by a volume selective excitation or other means. The volumetric trabecular density can therefore be derived from the following:

$$BV/TV = (Vt - TbN*Ev)/Vt. \quad (12)$$

These values of connectivity and volumetric trabecular density can be indicative of osteoporosis in the patient 104. Accordingly, a physician or technician can diagnose the patient 104 with osteoporosis and/or prescribe a treatment (e.g., medication) based at least in part upon such values.

In another exemplary approach, the bone structure model 304 can be characterized by its connectivity $\chi$, trabecular bone volume fraction BV/TV, and trabecular orientation $\theta$, as well as the ratio of rods to plates, the thickness of the plates or rods, and the variation in thickness of plates and rods. In this approach, the likelihood function 306 can be generated by numerically simulating a large number of random trabecular structures in three-dimensions with a given set of properties. By calculating the modulus of the Fourier transform of each of these and thereafter averaging the resultant values, a likelihood function for that set of properties can be obtained. This can be repeated for all possible properties to be tested, wherein the range of parameters tested can be defined by values observed in ex vivo measurements.

In yet another exemplary approach, the likelihood function 306 can be determined using a range of samples measured ex vivo, wherein the samples can be independently characterized using x-ray microtomography or some other technique to determine the true three-dimensional structure of each sample. From such results, a parameterized model can be developed. At least two exemplary approaches can be used: 1) the bone can be described as either osteo-poritic or not, and therefore the analysis reduces to a "yes" or "no" problem; 2)

the size, connectivity, and other key structure parameters can be assembled for each sample and likelihood curves can be derived for different combinations of these features.

When sampling from the MRI signal received from the MRI scanner, points in the Fourier domain that include useful information on a scale corresponding to a trabecular bone can be selectively sampled, thereby increasing signal-to-noise ratio. For instance, data can from the MRI signal can be acquired in k-space up to around 20,000 m$^{-1}$, while data close to k=0 m$^{-1}$ can be excluded as this data will largely describe structural changes on a much larger length scale that are not germane to the microstructure of the trabecular bone. Furthermore, to achieve high resolution data, the appropriate resolution can be selected and only points in the MRI signal in the Fourier domain that include signals characteristic of such resolution are measured. Accordingly, acquisition time is reduced and signal-to-noise ratio is increased.

In summary, the system 300 can receive MRI signals from the MRI scanner 100, wherein such signals can be a relatively small number of one-dimensional MRI scans (e.g., 3-20 MRI scans). The MRI signal can be selectively sampled based upon a desired resolution, and samples can be received by the bone strength determiner component 308. The bone strength determiner component 308 can output values that are indicative of strength of the trabecular bone of the patient 104 by evaluating the likelihood function 306 over the received signals. The likelihood function 306 is based at least in part upon the bone structure model 304, which can be derived through a simple modeling of bone phase marrow pockets, through simulation, or through data collected via ex vivo measurements.

Additionally, while the description above pertains to MRI signals from the MRI scanner 100, it is to be understood that the microstructure of trabecular bone can be characterized through utilization of other imaging techniques, including but not limited to computed tomography or other suitable tomography approach. In such approaches, signals are generated in the time domain. Accordingly, appropriate Fourier transforms can be employed to cause the signals to be represented in the Fourier domain, and thereafter the approach described above can be employed to characterize the microstructure of trabecular bone.

Figure 4:
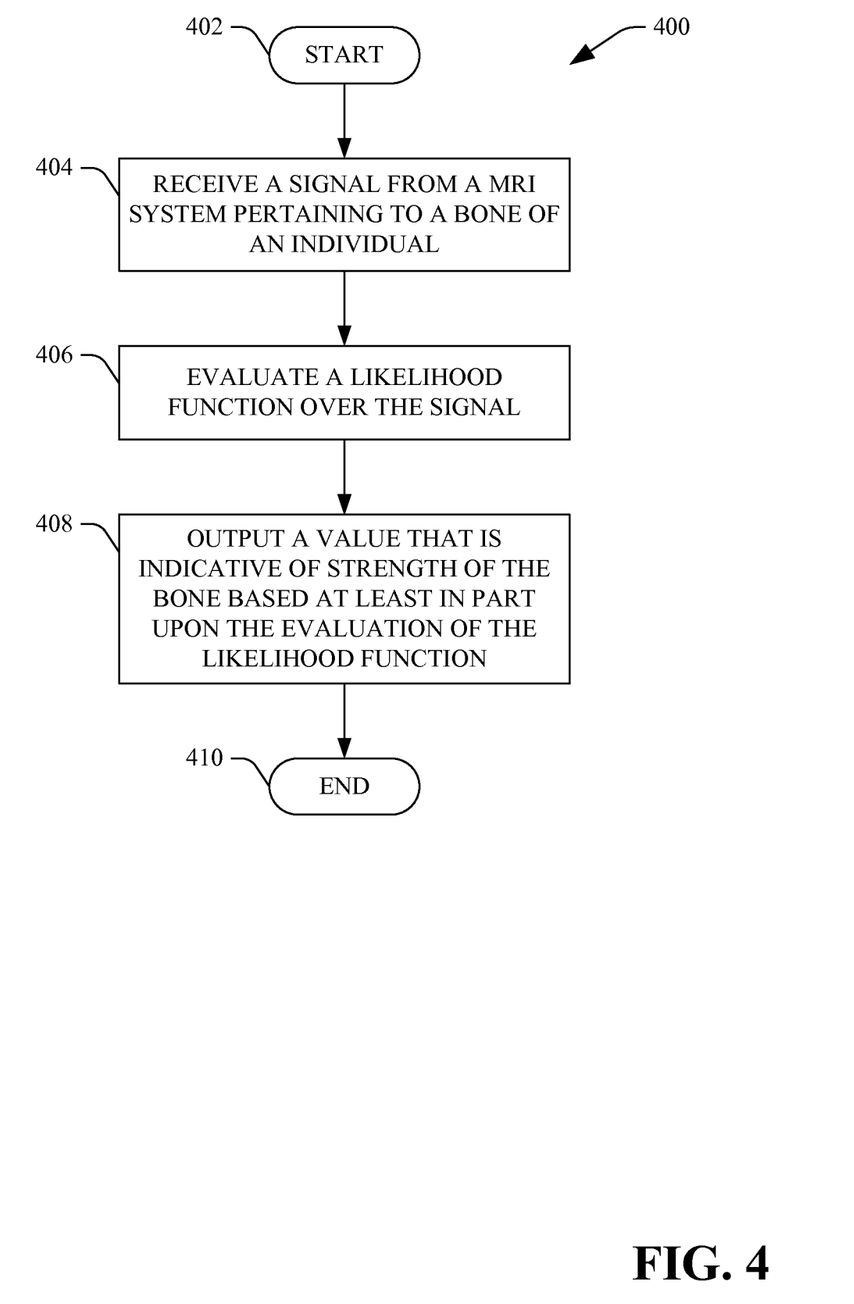
FIG. 4 is a flow diagram that illustrates an exemplary methodology for outputting a value that is indicative of strength of a bone.
Figure 5:
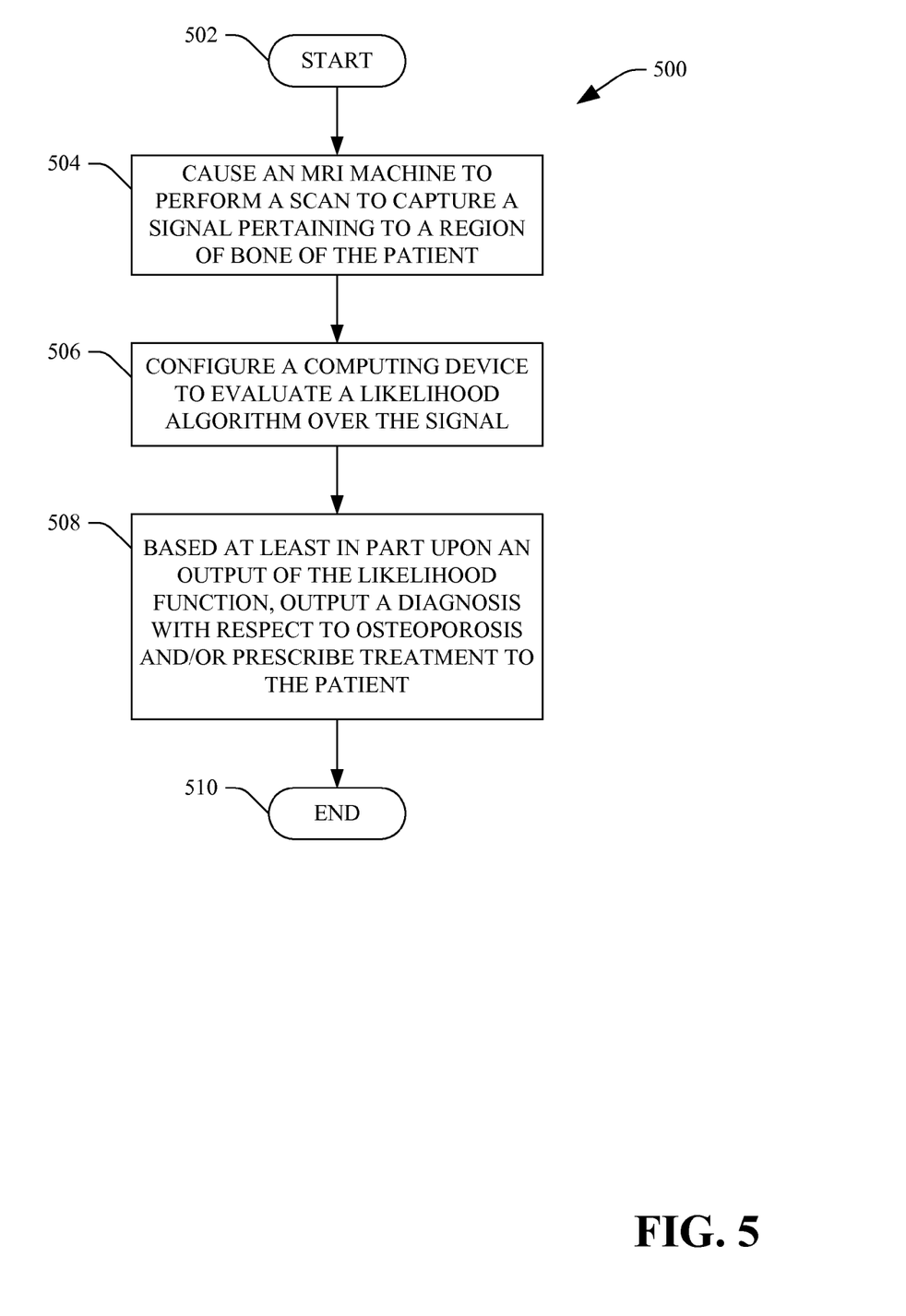
FIG. 5 is a flow diagram that illustrates an exemplary methodology for at least one of diagnosing or treating osteoporosis based at least in part upon a value output by a likelihood function.

With reference now to FIGS. 4-5, various exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Moreover, the acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodologies may be stored in a computer-readable medium, displayed on a display device, and/or the like. The computer-readable medium may be any suitable computer-readable storage device, such as memory, hard drive, CD, DVD, flash drive, or the like. As used herein, the term "computer-readable medium" is not intended to encompass a propagated signal.

Referring now to FIG. 4, a methodology 400 that facilitates generating data that is indicative of strength of a trabecular bone based at least in part upon an MRI scan is illustrated. The methodology 400 starts at 402, and at 404 a signal is received from an MRI system, wherein the signal is generated from a magnetic resonance scan of a bone of a patient. The signal can be selectively sampled to obtain data points that have a requisite resolution.

At 406, a likelihood function is evaluated over the data points, wherein the likelihood function is configured to output values that are indicative of strength of the trabecular bone. For instance, these values can be the size, aspect ratio, and orientation (and size distribution) of marrow phase pockets in the trabecular bone, which can be used to compute connectivity of the bone and volumetric trabecular density.

At 408, data is provided to an operator of the MRI system (e.g., a physician or technician) that is indicative of the strength of the bone of the patient. A physician may then generate a diagnosis of osteoporosis and/or prescribe treatment for osteoporosis based at least in part upon the values output at 408. The methodology 400 completes at 410.

With reference now to FIG. 5, an exemplary methodology 500 for diagnosing osteoporosis and/or prescribing treatment for osteoporosis is illustrated. The methodology 500 starts at 502, and at 504 an MRI machine is caused to perform a scan to generate a signal pertaining to a region of a bone of a patient of interest. At 506, a computing device is configured to evaluate a likelihood function over at least a portion of the signal, which is utilized to output values that are indicative of strength of the bone of the patient. At 508, a diagnosis of osteoporosis is made by a physician and/or treatment for osteoporosis is prescribed by the physician based at least in part upon the output the likelihood function. The methodology 500 completes at 510.

Figure 6:
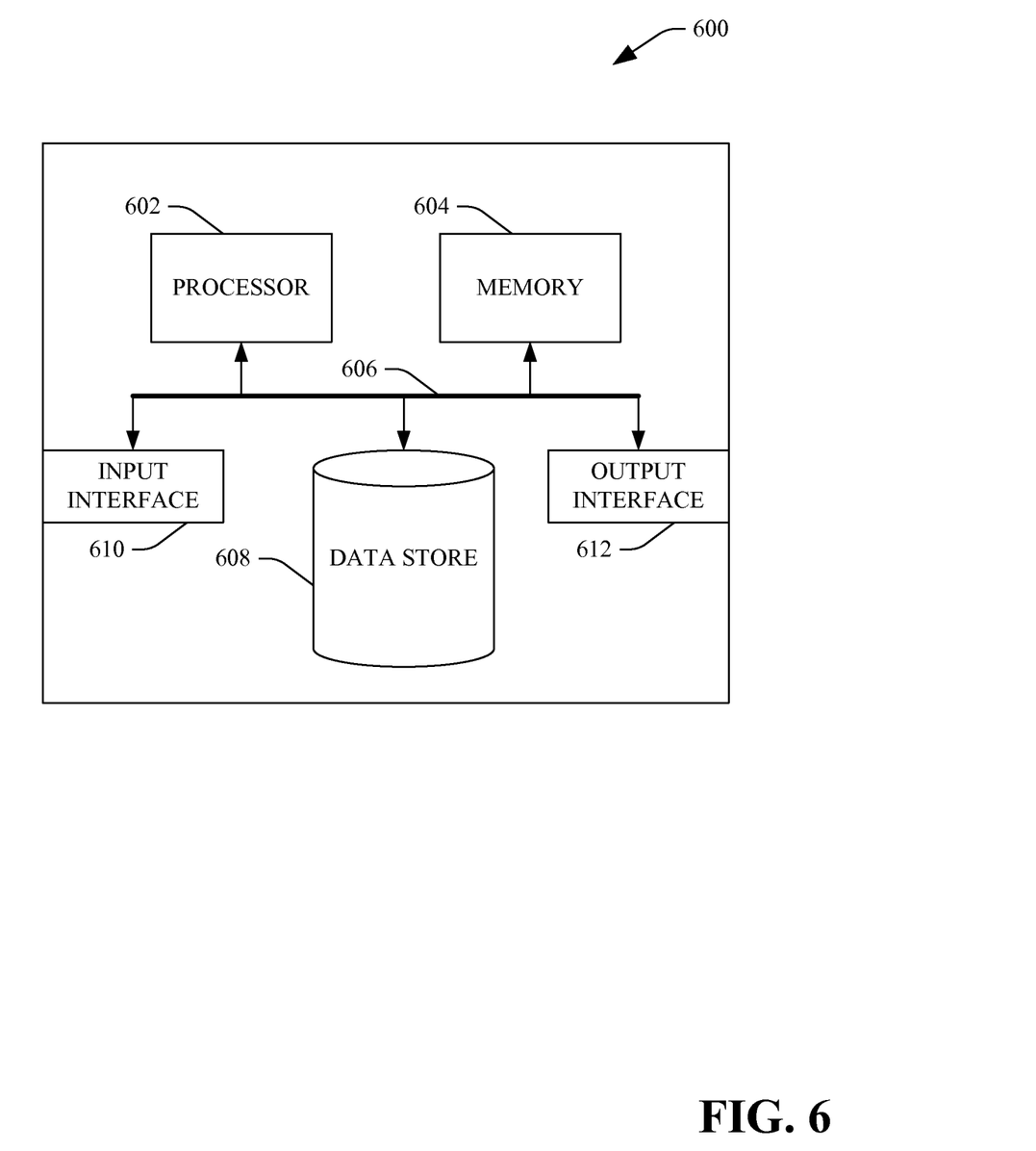
FIG. 6 is an exemplary computing system.

Now referring to FIG. 6, a high-level illustration of an exemplary computing device 600 that can be used in accordance with the systems and methodologies disclosed herein is illustrated. For instance, the computing device 600 may be used in a system that supports performance of MRI scans. The computing device 600 includes at least one processor 602 that executes instructions that are stored in a memory 604. The memory 604 may be or include RAM, ROM, EEPROM, Flash memory, or other suitable memory. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store MRI scans, a model of trabecular bone structure, etc.

The computing device 600 additionally includes a data store 608 that is accessible by the processor 602 by way of the system bus 606. The data store may be or include any suitable computer-readable storage, including a hard disk, memory, etc. The data store 608 may include executable instructions, MRI scan data, a model of a bone microstructure, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

Additionally, while illustrated as a single system, it is to be understood that the computing device 600 may be a distributed system. Thus, for instance, several devices may be in communication by way of a network connection and may collectively perform tasks described as being performed by the computing device 600.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. A method, comprising:
using a magnetic resonance imaging (MRI) system, performing one-dimensional magnetic resonance scans of a bone of a patient to generate signals, the magnetic resonance scans performed at multiple respective angles relative to the bone of the patient;
evaluating, by a processor, a likelihood function over the signals;
generating, by the processor, values that are indicative of size, aspect ratio, and orientation of marrow phase pockets of the bone of the patient based upon the evaluating of the likelihood function over the signals; and
providing data to an operator of the MRI system that is indicative of strength of the bone of the patient, the data based upon the values that are indicative of the size, aspect ratio, and orientation of the marrow phase pockets of the bone of the patient.

2. The method of claim 1, further comprising generating a value that is indicative of at least one of connectivity of the bone of the patient or volumetric trabecular density of the bone of the patient based upon the values that are indicative of the size, aspect ratio, and orientation of the marrow phase pockets of the bone of the patient, the data provided to the operator is based upon the value that is indicative of the at least one of connectivity of the bone of the patient or the volumetric trabecular density of the bone of the patient.

3. The method of claim 1, wherein the likelihood function is based upon a model of trabecular bone microstructure that comprises a model of marrow phase pockets of the trabecular bone microstructure.

4. The method of claim 3, further comprising modeling the marrow phase pockets of the trabecular bone microstructure as at least one of an ellipsoid model, a spherical model, a cuboid model, or a cylindrical model.

5. The method of claim 3, further comprising generating the model of the trabecular bone microstructure based upon ex vivo experiments on trabecular bones, the likelihood function based upon the model of the trabecular bone microstructure.

6. The method of claim 3, further comprising generating the model of trabecular bone microstructure based upon a plurality of numerical simulations, the likelihood function based upon the model of the trabecular bone microstructure.

7. The method of claim 1, the data provided to the operator is further indicative of a probability that the patient has osteoporosis.

8. The method of claim 1, wherein memory that is accessible to the processor comprises a computer-implemented model of trabecular bone microstructure, and wherein the likelihood function is evaluated over the signals by the processor based upon the computer-implemented model of the trabecular bone microstructure.

9. A system comprising:
a magnetic resonance imaging (MRI) scanner that is configured to generate magnetic resonance signals based upon respective magnetic resonance scans performed over a portion of a trabecular bone of a patient, the magnetic resonance scans performed at different angles with respect to the portion of the trabecular bone of the patient; and
a computing system comprising:
a processor; and
memory that comprises instructions that, when executed by the processor, cause the processor to perform a plurality of acts comprising:
performing a Bayesian analysis over the magnetic resonance signals; and
computing values that are indicative of size, aspect ratio, and orientation of marrow phase pockets of the trabecular bone based upon the Bayesian analysis performed over the magnetic resonance signals; and
displaying data on a display, the data based upon the values that are indicative of size, aspect ratio, and orientation of the marrow phase pockets of the trabecular bone.

10. The system of claim 9, wherein the acts further comprise:
computing a value that is indicative of connectivity of trabeculae in the trabecular bone based upon the values that are indicative of the size, the aspect ratio, and the orientation of the marrow phase pockets.

11. The system of claim 9, wherein the acts further comprise:
computing a value that is indicative of volumetric trabecular density of the trabecular bone based upon the values that are indicative of the size, the aspect ratio, and the orientation of the marrow phase pockets.

12. The system of claim 9, wherein performing the Bayesian analysis over the magnetic resonance signals comprises evaluating a likelihood function over the magnetic resonance signals.

13. The system of claim 12, wherein the memory comprises a computer-implemented model of trabecular bone microstructure, and wherein the likelihood function is evaluated based upon the computer-implemented model of the trabecular bone microstructure.

14. The system of claim 13, wherein the computer-implemented model of the trabecular bone microstructure comprises ellipsoids that model pockets of marrow phase.

15. The system of claim 13, wherein the acts further comprise:
constructing the computer-implemented model based upon data from ex vivo experiments on trabecular bone.

16. Computer-readable memory comprising instructions that, when executed by a processor, cause the processor to perform acts comprising:
causing an MRI scanner to perform a plurality of one-dimensional scans over a volume of trabecular bone of a patient to generate a plurality of signals, the plurality of one-dimensional scans conducted at different angles with respect to the volume of trabecular bone of the patient;
evaluating a likelihood function over a portion of each of the signals to generate a pair of values that are indicative of strength of the trabecular bone of the patient, the pair of values comprising a first value that is indicative of connectivity of trabeculae of the trabecular bone of the patient and a second value that is indicative of the trabecular bone volume fraction of the trabecular bone; and
based upon the pair of values, causing data to be output to a physician that is indicative of existence of osteoporosis in the trabecular bone of the patient.

17. The computer-readable memory of claim 16, the acts further comprising:
- evaluating the likelihood function over the portion of each of the signals to generate values that are indicative of size, aspect ratio, and orientation of marrow phase pockets in the trabecular bone of the patient; and
- generating the pair of values based upon the values that are indicative of the size, aspect ratio, and orientation of the marrow phase pockets.

18. The computer-readable memory of claim 17, wherein evaluating the likelihood function over the portion of each of the signals comprises evaluating the likelihood over the portion of each of the signals in k-space.

19. The computer-readable memory of claim 17, the acts further comprising:
- receiving a model of trabecular bone microstructure, the model including ellipsoids to model bone marrow pockets in the trabecular bone microstructure; and
- learning the likelihood function based upon the model of the trabecular bone microstructure.

20. The computer-readable memory of claim 17, the acts further comprising:
- sampling from the plurality of signals to generate the portion of each of the plurality of signals, the sampling based upon a predefined resolution.

* * * * *